United States Patent [19]

Straube et al.

[11] 4,376,438
[45] Mar. 15, 1983

[54] METHOD OF PRODUCING A SUPPORTING BANDAGE AND BANDAGING MATERIAL SUITABLE FOR THIS PURPOSE

[75] Inventors: Franz A. Straube; Günther Lehnert, both of Leverkusen, Fed. Rep. of Germany

[73] Assignee: Bayer Aktiengesellschaft, Leverkusen, Fed. Rep. of Germany

[21] Appl. No.: 254,681

[22] Filed: Apr. 16, 1981

Related U.S. Application Data

[63] Continuation of Ser. No. 968,657, Dec. 11, 1978, abandoned, which is a continuation of Ser. No. 785,794, Apr. 8, 1977, abandoned.

[30] Foreign Application Priority Data

Nov. 9, 1976 [DE] Fed. Rep. of Germany ....... 2651089

[51] Int. Cl.³ .............................................. A61F 5/04
[52] U.S. Cl. ......................................... 128/90; 427/2
[58] Field of Search ...................... 428/423.4; 128/90; 427/2

[56] References Cited

U.S. PATENT DOCUMENTS

| | | | |
|---|---|---|---|
| 2,650,212 | 8/1953 | Windemuth | 128/90 |
| 2,785,994 | 3/1957 | Lupfer | 428/447 |
| 3,015,585 | 1/1962 | Holbrook et al. | 428/266 |
| 3,307,537 | 3/1967 | Simon et al. | 128/90 |
| 3,317,481 | 5/1967 | Youker | 528/902 |
| 3,398,043 | 8/1968 | Youngs | 428/424 |
| 3,398,093 | 8/1968 | Youngs | 428/424 |
| 3,421,501 | 1/1969 | Beightol | 428/913 X |
| 3,582,423 | 6/1971 | Wang | 428/423 X |
| 3,617,367 | 11/1971 | Cummings | 428/423 |
| 3,630,194 | 12/1971 | Boardman | 128/90 |
| 3,635,904 | 1/1972 | Briggs et al. | 528/903 |
| 3,652,508 | 3/1972 | Segur et al. | 528/903 |
| 3,656,475 | 4/1972 | Hanrahan | 128/90 |
| 3,792,023 | 2/1974 | Havenith et al. | 260/77.5 AQ |
| 3,856,756 | 12/1974 | Wagner et al. | 260/77.5 AQ |
| 3,895,043 | 7/1975 | Wagner et al. | 260/448.8 R |
| 4,019,506 | 4/1977 | Eschmann | 128/90 |
| 4,020,832 | 5/1977 | Kirkpatrick | 128/90 |
| 4,046,744 | 9/1977 | Jenkins | 428/423 X |
| 4,131,114 | 12/1978 | Kirkpatricks | 427/2 X |

FOREIGN PATENT DOCUMENTS

| | | | |
|---|---|---|---|
| 625992 | 8/1961 | Canada | 428/266 |
| 2357931 | 11/1973 | Fed. Rep. of Germany . | |
| 2353212 | 4/1975 | Fed. Rep. of Germany | 128/90 |
| 2357931 | 5/1975 | Fed. Rep. of Germany . | |

OTHER PUBLICATIONS

Schweb, "Light Weight Foam Bandages in Medicine" Plastics, vol. 43, 1953.

*Primary Examiner*—Sam Silverberg
*Attorney, Agent, or Firm*—Sprung, Horn, Kramer & Woods

[57] ABSTRACT

The present invention relates to a process for producing a supporting bandage for surgical or veterinary surgical use comprising covering the part of the body which is required to be supported with an air-permeable dressing and then applying a self-hardening bandage over this dressing, characterized in that the self-hardening bandage comprise strips of air-permeable, flexible fabric coated and/or impregnated with about 50 to 300% by weight, based on the uncoated fabric, of an isocyanate prepolymer which contains free isocyanate groups and is based on aromatic polyisocyanates and polyols containing tertiary amino nitrogen atoms, the prepolymer having an isocyanate content of about 5 to 30% by weight and a tertiary amino nitrogen content of about 0.05 to 2.5% by weight, the coated fabric being soaked with water immediately before it is applied. The present invention also relates to lengths of bandaging material which comprise pieces of flexible, air-permeable fabric coated with about 50 to 300% by weight, based on the uncoated fabric, of an isocyanate prepolymer based on aromatic polyisocyanates and polyols containing tertiary amino nitrogen atoms, the isocyanate prepolymer having an isocyanate group content of about 5 to 30% by weight and a tertiary amino nitrogen content of about 0.05 to 2.5% by weight.

15 Claims, No Drawings

METHOD OF PRODUCING A SUPPORTING BANDAGE AND BANDAGING MATERIAL SUITABLE FOR THIS PURPOSE

This application is a continuation, of application Ser. No. 968,657, filed Dec. 11, 1978 now abandoned which itself is a continuation of Ser. No. 785,794, filed Apr. 8, 1977, now abandoned.

BACKGROUND OF THE INVENTION

It is known to use bandaging material impregnated with plaster of Paris for making stiff bandages. These plaster of Paris bandages are too heavy and insufficiently permeable to air and once set they rapidly lose their strength when moist, for example when brought into contact with water. Furthermore, owing to their capacity to absorb and scatter X-rays, they affect the diagnostic results of X-ray photographs and, owing to their inadequate resistance to water, they often give rise to skin irritation brought about by bacterial or mold growth in the bandage.

There have, therefore, been many attempts to provide bandaging materials which are free from these disadvantages. It has for example been attempted to impregnate bandaging material with polymer solutions which harden under exposure to UV light and then to harden the impregnated bandage by irradiation with UV lamp. (Chemical Orthopaedics and Related Research 103, 109–117 (1974)).

The UV lamps required for this purpose are difficult to handle, and moreover, the UV light only reaches the upper layers of the bandage so that the deeper layers harden only after a considerable time if at all. Another serious disadvantage of this method is that while the bandage is being hardened by UV light, the fracture under the bandage cannot be observed by X-rays.

A bandaging material which is capable of stiffening has been described in German Offenlegungsschrift No. 2,353,212. It consists of a flexible basic material treated with substances which contain oxycarbonyl isocyanate groups. The bandaging material described in German Offenlegungsschrift No. 2,353,212 was not successful in practice, partly because practically insurmountable difficulties were encountered in the manufacture of the bandaging material owing to the extremely high reactivity of oxycarbonyl isocyanates and partly because casts or supporting bandages made from these materials were not strong enough for the purposes required. Furthermore, the high reactivity of oxycarbonyl isocyanates rendered the impregnated bandaging material extremely unstable in storage since the prepolymers with oxycarbonyl isocyanate and urethane groups used according to German Offenlegungsschrift No. 2,353,212 rapidly harden even in the absence of atmospheric moisture.

The process described in German Offenlegungsschrift No. 2,357,931 for producing hardened bandages is also generally unsuitable for medical or surgical purposes because the process of hardening by the action of atmospheric moisture described in that Offenlegungsschrift takes too long.

The present invention provides a novel process for producing supporting bandages for surgical and veterinary surgical use which is substantially free from the disadvantages of the above mentioned processes known in the art. The process according to the invention described below is distinguished in particular by the following advantages:

1. The material is highly permeable to X-rays so that X-ray photographs can be taken through the bandage without any shadow
2. the bandages required for producing a given supporting effect are much lighter than the known plaster of Paris bandages providing the same effect, the saving in weight being up to about 80%;
3. the bandages are resistant to water;
4. the bandages attain weight bearing strength after only about 10 to 15 minutes;
5. the heat of reaction produced during hardening of the bandage is slight compared with that of conventional plaster of Paris bandages;
6. both application of the bandages and their removal after completion of the healing process are extremely simple and clean;
7. the risk of skin irritation due to bacteria or molds is much smaller than in known plaster of Paris bandages;
8. no apparatus is required for applying the bandage;
9. the bandages according to the invention have excellent permeability to air and hence breathing activity.

SUMMARY OF THE INVENTION

The present invention relates to a process for producing a supporting bandage for surgical or veterinary surgical use comprising covering the part of the body which is required to be supported with an air-permeable dressing and then applying a self-hardening bandage over this dressing, characterized in that the self-hardening bandage comprises strips of air-permeable, flexible fabric impregnated or coated with about 50 to 300% by weight, based on the uncoated fabric, of an isocyanate prepolymer which contains free isocyanate groups and is based on aromatic polyisocyanates and polyols containing tertiary amino nitrogen, the prepolymer having an isocyanate content of about 5 to about 30% by weight and a tertiary amine nitrogen content of about 0.05 to 2.5% by weight, the impregnated and/or coated fabric being soaked with water immediately before it is applied. Even the impregnation time is not critical, kneading water for 3 to 5 seconds is sufficient. Due to the short hardening time storage in water preferably should not exceed 2 minutes.

The present invention also relates to lengths of bandaging material which comprise pieces of flexible, air-permeable fabric coated and/or impregnated with about 50 to 300% by weight, based on uncoated fabric, of an isocyanate prepolymer which contains free isocyanate groups and is based on aromatic polyisocyanates and polyols containing tertiary amino nitrogen atoms, the isocyanate polymer having an isocyanate group content of about 5 to 30% by weight and a tertiary amino nitrogen content of about 0.05 to 2.5% by weight.

DETAILED DESCRIPTION OF THE INVENTION

To carry out the process according to the invention, the part of the body which is required to be supported is first covered with an air permeable, unimpregnated dressing. Suitable materials for this dressing include, for example, porous paper, non-woven webs or textile fabrics. The materials used for this dressing preferably have only a limited hydrophilic character. Non-woven polyester or polypropylene fabrics, for example, are therefore particularly suitable.

When the affected part of the body has been covered with the unimpregnated dressing, a bandage according to the invention which has previously been saturated with water is wound over it. This saturation with water of the bandaging material used according to the invention is carried out immediately before application of the bandage, for example, by immersing it in water.

The bandaging materials according to the invention are flexible, air-permeable fabrics having a weight per unit area of from about 20 to 1000 g/m$^2$, preferably about 30 to 500 g/m$^2$, which are impregnated with certain isocyanate prepolymers. The basic fabric of the bandaging material is preferably a textile. Suitable fabrics for this purpose include, for example, the following:

(1) Woven, knitted or warp knitted textile fabrics having a weight of about 20 to 200 g/m$^2$, preferably about 40 to 100 g/m$^2$ and a thread count of preferably about 2 to 20 threads per centimeter in the longitudinal and transverse direction. The woven or knitted textile fabric may be produced from any natural or synthetic yarn, but it is preferred to use fabrics made of mixed yarns containing both hydrophobic filaments or fibers with a high elastic modulus (for example polyester) and hydrophilic natural or synthetic filaments or fibers (for example cotton or polyamide).

(2) Woven, knitted or warp knitted glass fiber fabrics weighing from about 60 to 500 g/m$^2$, preferably about 100 to 400 g/m$^2$ and having a thread count of preferably about 2 to 20 per centimeter in the longitudinal and transverse direction. Glass fiber fabrics which have been treated with a hydrophilic sizing agent are preferred.

(3) Bonded or non-bonded or stitched non wovens based on inorganic and preferably organic fibers and having a weight of about 30 to 400 g/m$^2$ preferably about 50 to 200 g/m$^2$.

For producing stiff bandages according to the invention in the form of shells or splints, it is also suitable to use textile materials (preferably non-wovens) of the kind mentioned above weighing up to about 1000 g/m$^2$.

The woven, knitted or warp knitted fabrics mentioned under paragraph (1) above are particularly preferred.

Isocyanate prepolymers suitable for impregnating the flexible fabrics mentioned above as examples include in particular those which have from about 5 to 30% by weight, preferably about 10 to 25% by weight, of aromatically bound isocyanate groups and about 0.05 to 2.5% by weight, preferably about 0.1 to 1.5% by weight, of tertiary amino nitrogen atoms. Furthermore, suitable choice of the viscosity of the starting materials used for preparing the isocyanate prepolymers ensures that the prepolymers have a viscosity of from about 5000 to 50,000 cP at 25° C., preferably about 10,000 to 30,000 cP at 25° C.

The preparation of the isocyanate prepolymers is carried out in known manner by reacting excess quantities of aromatic polyisocyanates with polyols which contain tertiary amino nitrogen atoms, preferably at an NCO/OH-ratio of between 2:1 and 15:1.

The aromatic polyisocyanates used may be any of the aromatic polyisocyanates known in polyurethane chemistry which have been described, for example, in "Polyurethanes, Chemistry and Technology", Part I, Interscience Publishers (1962) or in "Kunststoff-Handbuch", Volume VII, Polyurethane, Carl Hanser Verlag, Munich (1966). The following are preferred: 2,4-diisocyanatotoluene or 2,6-diisocyanatotoluene or isomeric mixtures thereof; 4,4'-diisocyanatodiphenylmethane and 2,4'-diisocyanatodiphenylmethane and mixtures of these isomers which may contain small quantities of 2,2'-diisocyanatodiphenylmethane, or any mixtures of the above mentioned polyisocyanates or polyisocyanate mixtures which can be obtained by the phosgenation of aniline-formaldehyde condensates and which contain higher nuclear diphenylmethane polyisocyanates in addition to 2,2'- 2,4'- and 4,4'-diisocyanatodiphenylmethane. The last mentioned diphenylmethane polyisocyanate mixtures are particularly preferred.

The following are examples of suitable polyols containing tertiary amino nitrogen atoms:

(1) Low molecular weight polyols having a molecular weight of from about 105 to 300 which contain tertiary nitrogen atoms and are free from ether groups, e.g. N-methyl-diethanolamine, N-ethyldiethanolamine, N-methyl-dipropanolamine, triethanolamine or tripropanolamine;

(2) polyester polyols having a molecular weight of from about 300 to 2000, preferably about 800 to 1500, containing tertiary nitrogen atoms, which polyester polyols can be obtained by the reaction of polybasic acids with amino alcohols of the kind mentioned in (1) above as examples, if desired together with polyhydric alcohols which are free from nitrogen. Suitable polybasic acids include, for example, adipic acid, phthalic acid and hexahydrophthalic acid. Suitable nitrogen free polyhydric alcohols for the preparation of the polyesters include, for example, ethylene glycol, tetramethylene glycol, hexamethylene glycol and trimethylolpropane.

(3) Polyether polyols with tertiary amino nitrogen atoms having a molecular weight of from about 300 to 2000, preferably about 800 to 1500, which can be obtained in known manner by the alkoxylation of nitrogen containing starting compounds. Suitable starting compounds of this kind include, for example, ammonia, the amino alcohols mentioned in (1) above as examples and amines containing at least two-NH-bonds, e.g. ethylene diamine, aniline and hexamethylenediamine. Suitable alkylene oxides for the preparation of the polyethers include, for example, ethylene oxide and propylene oxide. Propoxylation products of the above mentioned nitrogen containing starting materials are particularly preferred.

Any method may be used for coating and/or impregnating the bandaging materials used in the process according to the invention with the above mentioned isocyanate prepolymers. Conventional apparatus or devices may be used, for example the bandages may be coated by means of doctor coat wipers or impregnated and subsequently squeezed off on rollers or centrifuged or they may be sprayed with the isocyanate prepolymer.

The prepolymer may be used either solvent-free or as a solution. In the case of a solution, the preferred solvents are volatile solvents such as methylene chloride, acetone, methyl ethyl ketone, chloroform, THF, ethyl acetate, chlorobenzene and DMF.

Preferably the weight per unit area, density of mesh of the flexible support and quantity of isocyanate prepolymer applied within the ranges specified above are chosen so that only the fibers of the fabric become coated with the impregnating agent while gaps between the fibers are preserved to ensure the necessary porosity to air.

If auxiliary solvents have been used, the impregnated substrate is subsequently freed from them, for example, by a vacuum treatment. After impregnation, the resulting bandaging materials according to the invention may be stored in sealed containers in the absence of moisture. They are preferably stored as rolls or folded flat in airtight metal containers, for example aluminum containers. Sealed bags made of polyethylene coated aluminum foils or moisture sealed aluminum tins are particularly suitable for storing the bandages according to the invention.

One of the advantages of the bandaging materials according to the invention, compared with the bandaging materials according to German Offenlegungsschrift No. 2,353,212 is that when packed airtight as described above they can be stored under normal conditions.

Whenever the bandaging materials are required for the process according to the invention, they can be removed from the container and impregnated with water. The thickness of the supporting bandage (e.g. splint or cast) formed by the process according to the invention depends on the surgical requirements and is generally between about 3 and 10 mm. The bandaging materials according to the invention may be used in the process according to the invention both for forming supporting bandages or casts by winding the strips of material around the parts of the body which require support or they may be used as flat folded bandages for forming shells or splints.

The bandaging materials may be colored, for example, by the addition of pigments or dyes to the isocyanate prepolymers. To increase the rigidity of the supporting bandages formed according to the invention, inorganic additives which may be chemically inert or capable of hardening under the action of water may be added to the isocyanate prepolymers used for impregnating the bandaging materials, but the use of such additives is generally unnecessary due to the excellent mechanical properties of the supporting bandages obtained by the process according to the invention. Suitable additives would be, for example, chalk, glass fibers or plaster of Paris.

The invention is further illustrated, but is not intended to be limited by the following examples in which all parts and percentages are by weight unless otherwise specified.

EXAMPLES

Example 1

A strip of bandage gauze made of bleached cotton 12 cm in width and 4 m in length and having a weight of 31 g/m$^2$ and a thread count of 11 threads per cm in the longitudinal direction and 8 threads per cm in the transverse direction of the woven fabric is impregnated with 24 g of an isocyanate prepolymer obtained from (a) a phosgenation product of an aniline-formaldehyde condensate having an isocyanate group content of about 30% by weight and a viscosity of 200 cP at 25° C. and (b) a trihydroxypolyether obtained by propoxylation of triethanolamine and having an OH number of 146 and a viscosity of 1200 cP/25° C. in a ratio by weight of a:b=3:1 (tertiary N: 0.3% by weight; free isocyanate group content: 18.7% by weight; viscosity: 21,300 cP at 25° C.) on impregnating rollers with stringent exclusion of atmospheric moisture (dew point below −50° C.), and the impregnated guaze is wound on a core of polyethylene and sealed into a bag made of a three-layered laminate of polyester, aluminum and polyethylene equipped with a sealing edge.

When it has been stored for one week at about 25° C., the impregnated bandaging material is removed from its package, dipped in water at about 25° C. for 3 to 5 seconds and lightly kneaded. It is then wound within 3 minutes around a tubular body having an internal diameter of 42 mm and a length of about 12 cm.

The supporting bandage hardens within a further 5 minutes with slight evolution of heat (maximum surface temperature 35° C.) to form a stable, solid structure which is capable of bearing loads and has excellent bonding between the layers.

Example 2

30 impregnated strips of bandaging material are prepared by the process described in Example 1 and tested for use after storage at about 25° C. for 3, 6 and 9 months. In the bending test (width of unsupported material 40 mm, maximum bending load 50 kp), the test samples obtained as described in Example 1 show a maximum deviation of the deformation due to load of ±10%, which is within the range of deviations due to manufacture found in such hand finished test samples. No fracture of the test samples under load occurred up to the maximum load.

Example 3

The process described in Example 1 was repeated but instead of the 4 m long strip of bandage gauze, a 2 m long strip of warp knitted fabric (width 10 cm) made of a mixed yarn of 67% polyester fibers and 33% cotton fibers and having a weight of 97 g/m$^2$ and a thread count of 4 threads per cm in the longitudinal direction and 10 threads per cm in the transverse direction was used. The ratio by weight of the isocyanate prepolymer described in Example 1 to the weight of fabric was 1.4:1. A sample prepared by the process according to Example 1 hardened within 6 to 7 minutes and in the mechanical test it showed the same rigidity as a sample produced from twice the length of fabric by the method described in Example 1.

Example 4

A strip of bandage guaze 12 cm in width produced from a mixed yarn of 40% cotton and 60% viscose and weighing 30 g/m$^2$ and having a thread count of 12 threads per cm in the warp and 8 threads per cm in the weft is impregnated with 25 g of the isocyanate prepolymer described in Example 1 in the form of a solution in methylene chloride (ratio by weight of prepolymer/solvent=1/1) under moisture free conditions, and the solvent was removed by an oil pump vacuum. The resin impregnated bandaging material was packaged as in Example 1 and stored for about one month at about 25° C. The package was opened at the end of this time and a test sample is produced as in Example 1. The setting time and strength of the sample are similar to those of the sample obtained in Example 1.

Example 5

45 strips of bandaging material were prepared and packaged as in Example 4. Over a period of three months, the strips were used in clinical tests for preparing surgical supporting bandages or casts on the upper and lower extremities of patients with fractures of the long bones. The dressing used under the bandages was a polyester fleece or cotton wadding about 0.4 cm in thickness. The bandages hardened within a maximum of 10 minutes and were load bearing after only one hour.

The supporting bandages could be applied without soiling the surgery and could be exactly modelled. There was no need to remove the bandages for X-ray examination of the fracture since they caused no shadow on X-ray films. They were radiologically practically invisible.

The bandages were removed with the aid of the usual tools used for plaster casts (plaster shears, oscillating saw). The bandages without exception produced very little dust compared with plaster casts. All the patients found the very low weight of the bandages and the porosity to air extremely pleasant.

The condition of the skin areas which had been covered by the bandages was extremely satisfactory in all cases. No allergic reactions were observed.

Example 6

Strips of woven glass fiber fabric 1 m in length and about 10 cm in width and weighing 285 g/m² and having a thread count of 20 threads per cm in the warp and 6 threads per cm in the weft were impregnated with the isocyanate prepolymer described in Example 1 by the process according to Example 4. The quantity of prepolymer applied was 150 g/m². Tubular test samples having the dimensions described in Example 1 were prepared by hand as in Example 1 and tested for bending. No fracture could be produced under a load of 50 kp. The maximum sagging obtained under the test conditions of Example 2 was 4 mm.

Example 7

A strip of glass silk fabric 2.3 m in length and 10 cm in width and having a thread count of 20 threads per cm in the warp and 6 threads per cm in the weft and weighing 290 g/m² was impregnated by the process described in Example 4 with 69 g of the prepolymer described in Example 1. The impregnated length of fabric was then folded to a length of about 8 cm and packed airtightly into a tin under exclusion of moisture. When the packaging material was removed from its package after several months of storage, it showed no signs of change. It was placed in water at a temperature of 20° C. for about 2 minutes and then spread out on a polyethylene foil to form six layers of equal length placed above one another. After about 3 minutes, the viscosity of the PU resin applied to the fabric increased sharply with moderate rise in temperature. While in this condition, the stack of bandaging material was applied to the forearm of a patient to form a supporting half shell for the wrist and forearm. The hardening reaction was substantially completed after a further two minutes. The dimensionally stable half shell was then placed inside a circular stiffening bandage for added rigidity.

Example 8

Strips of a stitched non-woven of polyester fibers measuring 10×25 cm in width and length and about 4 mm in height and weighing 820 g/m² were impregnated with 240% by weight, based on the weight of the textile, of the PU prepolymer described in Example 1 by the method of solution impregnation described in Example 4. The impregnated strips were dipped in water at a temperature of about 40° C. for about one minute and used immediately for modelling a half shell on a human forearm after the usual application of a dressing to the skin. The bandage had hardened substantially completely after about 5 minutes.

The case obtained in this way was perforated mechanically to make it permeable to air and used as surgical forearm splint.

Example 9

The strips of bandaging material specified in Example 3 were impregnated by the method of solution impregnation described in Example 4 with an isocyanate groups containing prepolymer obtained from (a) a phosgenation product of an aniline-formaldehyde condensate having an isocyanate group content of about 30% by weight and a viscosity of 100 cP at 25° C. and (b) a polyether obtained by propoxylation of ethylene diamine and having a molecular weight of 1140 and an OH number of 196, in proportions by weight of a:b=4:1 (viscosity of the prepolymer 15,400 cP at 25° C.; free isocyanate content 20.4% by weight, tertiary nitrogen: 0.24% by weight).

When the bandaging material was made up into test samples as described in Example 1, they hardened within about 8 minutes. In the mechanical tests, the samples were found to have exceptionally high impact strengths.

Example 10

Numerous strips of bandaging material were prepared for use as stiffening bandages by the process according to Example 4 and made up into test samples. The samples were stored in groups of 4 (length of fabric 4 m, width of fabric 10 cm) in 1 liter of twice distilled water for 4 hours at 23° C. and 2 hours at 50° C., and the aqueous extracts were examined for their carbon content after filtration. The carbon content was found to be between about 0.002 and 0.007% by weight, showing that the hardened bandages release practically no organic material when moist.

Example 11

Strips of bandaging material conforming to the specifications given in claim 1 were prepared by the process according to Example 1 and made up into test samples as described. Some of the test samples were tested for their flexural strength and breaking strength after about 24 hours. Another portion of the test samples were stored in water at about 20° C. for 2 hours, dried and then tested under loads of up to a maximum of 50 kp for comparison with the test samples mentioned above. The decrease in strength after storage in water was insignificant within the limits of statistical error. This indicates that showers or baths can be taken when wearing the supporting bandage according to the invention.

Example 12

A cotton bandage gauze 12 cm in width conforming to the specifications given in Example 1 was impregnated by the process described in Example 4 with an isocyanate prepolymer obtained from a mixture of 4,4'-diphenylmethane diisocyanate and 2,4'-diphenylmethane diisocyanate (proportions by weight 1:1.5) and a propoxylated triethanolamine having a molecular weight of about 1200 and an OH number of 146 in proportions by weight of the diisocyanates to the propoxylated triethanolamine of 1.25:1, in a manner analogous to the process of Example 1. The prepolymer contained about 12% of free isocyanate groups and had a viscosity of 19,000 cP at 25° C.

Test samples prepared in a manner analogous to Example 1 were completely hardened after only 5 minutes, had sufficient mechanical strength for surgical use and were highly permeable to air and moisture.

Example 13

A strip of bandaging fabric 10 cm in width and 4 m in length manufactured from a mixed yarn of 65% polyester and 35% cotton and having a weight of 60 g/m$^2$ and a thread count of 12 threads per cm in the warp and 8 double threads per cm in the weft was impregnated with about 160% by weight, based on the weight of the textile, of the isocyanate prepolymer described in Example 12, and sealed into a polyethylene coated aluminum bag with sealed edge. After 9 months in storage at an average temperature of 23° C., the bandaging fabric was used for preparing a test sample as in Example 1. When the impregnated fabric was made up into a test sample and mechanically tested, no significant differences in properties were found between test samples of freshly prepared bandaging material and the above described test samples.

Example 14

Strips of tubular knitted fabric 50 cm in length and 10.5 cm in width when laid out flat made of untextured polyacrylonitrile yarn and having an open mesh of about 1 mm$^2$ and a weight of 238 g/m$^2$ (when double) were impregnated each with 12 g of the prepolymer described in Example 1 by the method according to Example 4 and made up into test samples of the kind described in Example 1, using the tubes as double layered bandaging fabric. The hardening time was approximately 7 minutes. The test samples had good breathing activity and excellent bonding between the layers so that the hardened bandages could not be unwound without destroying the textile structure.

Example 15

Numerous strips of bandaging fabric 4 m in length conforming to the specifications given in Example 13 were impregnated with the PU prepolymer described in Example 1 by the method according to Example 4. The quantities of prepolymer applied were 104, 156 and 208% by weight, based on the weight of the dry, unimpregnated fabric.

The base of a transparent tube 30 cm in length and 0.9 cm in diameter was glued to the test samples and the outflow time of a water column 10 cm in height was measured.

The outflow time through fabrics which had been impregnated with 104% by weight and 156% by weight was approximately 3 seconds; when the fabrics were impregnated with 208% by weight, the outflow time increased to approximately 10 minutes.

This test demonstrates the excellent breathing activity of bandaging fabrics which have been impregnated with the optimum amount of 150 to 160% by weight. In the case of the least impregnated fabric (104%), the test sample was destroyed in the bending test under a load of only 35 kp while more highly impregnated test samples remained completely intact under a load of 50 kp and were deformed by only about 2 mm.

Example 16

(Comparison Example)

Numerous strips of bandage gauze described in Example 4 were impregnated each with 25 g of trimeric hexamethylene diisocyanate by the method indicated in Example 4. The impregnated bandaging fabrics were kneaded for 10 seconds in water at 20° C. and made up into tubular test samples having a length of about 12 cm and an internal diameter of 42 mm. The time required for complete hardening at about 23° C. was about 48 hours.

In another test series, 0.3% by weight of tertiary nitrogen in the form of N,N-dimethylaniline was added as activator to the polyisocyanate. The test samples obtained in this series showed no significant reduction in the hardening time but had an unpleasant odor due to free amine.

In another test series, N,N'-dimethylaminoethane was used as activator instead of N,N-dimethylaniline. Test samples prepared from the bandaging fabrics in this series did not harden significantly more rapidly than the starting material. These were also found to have an unpleasant odor.

EXAMPLE 17

(Comparison Example)

Strips of bandage gauze confirming to the specification given in Example 4 were impregnated with an isocyanate prepolymer of (a) a phosgenation product of an aniline-formaldehyde condensate having an isocyanate group content of about 30% by weight and a viscosity of 100 cP at 25° C. and (b) a polypropylene glycol polyether which had been started with moist glycerol and had an OH number of 159, a molecular weight of 920 and a functionality of 2.62 by the method described in Example 4. The ratio by weight of a:b was 3:1. The prepolymer was found to have a viscosity of 12,600 cP at 25° C. and to contain 20.4% by weight of free isocyanate groups.

After storage in sealed polyethylene-aluminium-polyester bags, the strips of bandaging fabric were made up into test samples by the method described in Example 1 and their hardening time was determined. This was in all cases more than 45 minutes, which indicated that the prepolymer system free from activator was unsuitable for use as surgical supporting bandage or cast.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of a rigid supporting bandage for surgical or veterinary surgical use which attains weight bearing strength in from five to about fifteen minutes comprising covering the part of the body which requires support with an air-permeable dressing and then applying a self-hardening bandage, characterized in that the self-hardening bandage comprises strips of air-permeable, flexible bandaging fabric which have been impregnated and/or coated with about 50 to 300% by weight, based on the uncoated fabric, of an isocyanate prepolymer which contains free isocyanate groups and has been prepared from aromatic polyisocyanates and polyols containing tertiary amine nitrogen atoms, the prepolymer having an isocyanate content of about 5 to 30% by weight and a tertiary amino nitrogen content of about 0.05 to 2.5% by weight, the impregnated and/or coated bandaging fabric being soaked with water immediately before its use.

2. Strips of bandaging material suitable for carrying out the process according to claim 1, characterized in that they comprise flexible, air-permeable pieces of fabric which have been impregnated and/or coated with about 50 to 300% by weight, based on the uncoated fabric, of an isocyanate prepolymer based on aromatic polyisocyanates and polyols containing tertiary amino nitrogen atoms, the isocyanate prepolymer having an isocyanate group content of about 5 to 30% by weight and a tertiary amino nitrogen content of about 0.05 to 2.5% by weight, said bandaging material being capable of attaining weight bearing strength in less than about fifteen minutes after being soaked with water.

3. The bandaging material of claim 2 wherein the air-permeable pieces of fabric have a weight per unit area of from about 20 to 1,000 g/m$^2$.

4. The bandaging material of claim 2 wherein the isocyanate prepolymer has a viscosity of from about 5000 to 50,000 cP at 25° C.

5. The bandaging material of claim 2 wherein the isocyanate prepolymer has an isocyanate group content of about 10 to 25% by weight and a tertiary amino nitrogen content of about 0.1 to 1.5% by weight.

6. The bandaging material of claim 2 wherein the isocyanate prepolymer is applied in solvent free form.

7. The bandaging material of claim 2 wherein the isocyanate prepolymer is applied in solution form.

8. The bandaging material of claim 2 wherein the isocyanate prepolymer is based on aromatic polyisocyanates which are the phosgenation product of aniline-formaldehyde condensates and polyether polyols having tertiary amino nitrogen atoms and having a molecular weight of from about 300 to 2,000.

9. A process for the preparation of a rigid supporting bandage which attains weight bearing strength in from five to about fifteen minutes comprising
  (A) applying an air-permeable dressing to a structural unit which needs support, and
  (B) applying a self-hardening bandage to the air-permeable dressing, said self-hardening bandage comprising strips of an air-permeable, flexible bandaging fabric which have been impregnated and/or coated with about 50 to 300% by weight, based on the uncoated fabric, of an isocyanate prepolymer, said isocyanate prepolymer
    (1) being based on aromatic polyisocyanates and polyols containing tertiary amino nitrogen atoms,
    (2) having an isocyanate group content of about 5 to 30% by weight,
    (3) having a tertiary amino nitrogen content of about 0.05 to 2.5% by weight, and
    (4) having a viscosity of from about 5000 to 50,000 cP at 25° C. wherein said self-hardening bandage is soaked with water immediately before its application.

10. A medical supporting material which attains weight bearing strength in from five to about fifteen minutes after being soaked with water comprising flexible air-permeable pieces of fabric which have been impregnated and/or coated with about 50 to 300% by weight, based on the uncoated fabric, of an isocyanate prepolymer based on aromatic polyisocyanates and polyols containing tertiary amino nitrogen atoms, the isocyanate prepolymer having an isocyanate group content of about 5 to 30% by weight and a tertiary amino nitrogen content of about 0.05 to 2.5% by weight.

11. A medical supporting material which attains weight bearing strength in from five to about fifteen minutes after being soaked with water enclosed in a moisture free and moisture-impervious container comprising flexible, air-permeable pieces of fabric which have been impregnated and/or coated with about 50 to 300% by weight, based on the uncoated fabric, of an isocyanate prepolymer based on aromatic polyisocyanates and polyols containing tertiary amino nitrogen atoms, the isocyanate prepolymer having an isocyanate group content of about 5 to 30% by weight and a tertiary amino nitrogen content of about 0.05 to 2.5% by weight.

12. A process for the preparation of a rigid supporting bandage for surgical or veterinary surgical use which attains weight bearing strength in between about 5 and 15 minutes comprising covering the part of the body which requires support with an air-permeable dressing and then applying a self-hardening bandage wherein the self-hardening bandage is prepared by impregnating or coating solvent free strips of air-permeable, flexible bandaging fabric with about 50 to 300% by weight, based on the weight of the untreated fabric, of a solvent free isocyanate prepolymer which contains free isocyanate groups and has been prepared from aromatic polyisocyanates and polyols containing tertiary amino nitrogen atoms at an NCO to OH ratio of between about 2:1 and 15:1, the prepolymer having an isocyanate content of about 5 to 30% by weight and a tertiary amino nitrogen content of about 0.05 to 2.5% by weight, the self-hardening bandage being soaked with water immediately before its use.

13. A medical supporting material which attains weight bearing strength in between about 5 and 15 minutes after being soaked with water enclosed in a moisture free and moisture impervious container comprising substantially solvent free flexible, air permeable pieces of fabric, which have been coated or impregnated with about 50 to 300% by weight, based on the weight of untreated fabric, of an isocyanate prepolymer, said prepolymer
  (a) being the reaction product of aromatic polyisocyanates and polyols containing tertiary amino nitrogen atoms prepared with an NCO to OH ratio of between 2:1 and 15:1,
  (b) having an isocyanate group content of 5 to 30% by weight, and
  (c) having a tertiary amino nitrogen content of about 0.05 to 2.5% by weight.

14. The medical supporting material of claim 13 wherein the polyol containing the tertiary amino nitrogen is the ethoxylation or propoxylation product of ammonia, an amine or an amino alcohol.

15. A medical supporting material which hardens substantially completely in between about five and fifteen minutes after being soaked with water enclosed in a moisture free and moisture impervious container comprising substantially solvent free flexible, air permeable pieces of fabric, which have been coated or impregnated with about 50 to 300% by weight, based on the weight of untreated fabric, of an isocyanate prepolymer, said prepolymer (a) being the reaction product of aromatic polyisocyanates and polyols containing tertiary amino nitrogen atoms prepared with an NCO to OH ratio of between 2:1 and 15:1, (b) having an isocyanate group content of 5 to 30% by weight, and (c) having a tertiary amino nitrogen content of about 0.05 to 2.5% by weight.

* * * * *